United States Patent [19]

Burns

[11] 4,112,931
[45] Sep. 12, 1978

[54] TIDAL VOLUME DISPLAY

[75] Inventor: Henry L. Burns, St. Helena, Calif.

[73] Assignee: Cavitron Corporation, New York, N.Y.

[21] Appl. No.: 757,129

[22] Filed: Jan. 5, 1977

[51] Int. Cl.² ............................................. A61B 5/08
[52] U.S. Cl. ................................ 128/2.08; 128/145.8; 128/DIG. 17; 128/DIG. 29
[58] Field of Search ................... 128/2.08, 2.07, 145.6, 128/145.8, DIG. 17, DIG. 29; 272/99

[56] References Cited

U.S. PATENT DOCUMENTS

| | | | |
|---|---|---|---|
| 3,033,195 | 5/1962 | Gilroy et al. | 128/145.8 |
| 3,875,626 | 4/1975 | Tysk et al. | 128/2.08 |
| 3,898,987 | 8/1975 | Elam | 128/145.8 |
| 3,961,627 | 6/1976 | Ernst et al. | 128/145.8 |

FOREIGN PATENT DOCUMENTS 491,375  2/1976  U.S.S.R. ................................. 128/2.08

Primary Examiner—Lee S. Cohen

Attorney, Agent, or Firm—William R. Evans; Robert M. Skolnik

[57] ABSTRACT

A breath volume indicating system has a regulator controlling the flow of gas from a source of gas under pressure to a supply system delivering the gas under pressure to a patient as well as to a chamber providing a fixed volume to receive a supply of the gas. The regulator includes two valves respectively operatively associated with the supply system and the chamber, each valve being operable simultaneously between closed and open positions. In the closed position of the valves, generally coinciding with an inhalation period of the patient, the regulator provides a flow of the gas to the patient through the supply system and into the chamber, concurrently, and, in the open position, generally coinciding with the exhalation period of the patient venting of the supply system (and thereby the patient) and the chamber, concurrently. The regulator further includes gas flow control orifices such that a gauge operatively connected to the chamber indicates a tidal volume that is directly equivalent of the volume of the gas directed to the patient through the supply system during the patient's inhalation period when the valves are closed.

44 Claims, 1 Drawing Figure

TIDAL VOLUME DISPLAY

BACKGROUND OF THE INVENTION

1. Field of the Invention

The present invention relates to monitoring the breathing of medical patients, and more particularly to devices and methods for indicating instantaneously the tidal volume of each patient breath.

2. Description of the Prior Art

Efficient utilization of the typical respiratory system ventilator is frequently impaired by the lack of immediate information regarding the tidal volume delivered with each inhalation cycle. It is a common practice in ventilator design to direct a regulated constant flow of gas past a patient interface and out to ambient air through an exhalation valve. When the patient inhales by his own effort he merely diverts part of the gas flow into his lungs during his inhalation cycle. When it is desired that the ventilator supply the inhalation energy, the exhalation valve is programmed to open and close intermittently to force inhalation whenever the exhalation valve is closed.

If the flow rate and the time of exhalation valve closure are known, the force-inhalation tidal volume can be calculated. This tidal volume calculation requires an accurate flow measuring and indicating device, an accurate time measuring and indicating device and an accurate calculating capability. Even if the accurate flow and time measuring and indicating devices are provided, the calculation must be performed any time the flow rate of inhale cycle time is changed, and the net result in practice is to ignore the tidal volume parameter or to avoid making a flow and/or time change that might optimize the ventilator-patient interchange.

The need for an accurate and sensitive tidal volume indicator has thus existed for some time, and attempts to provide one are illustrated in U.S. Pat. Nos. 3,789,837 and 3,898,987. A review of the disclosure in these patents however, illustrates the complicated arrangements previously arrived at. For example, in U.S. Pat. No. 3,898,987 a bag is expanded and collapsed in timed relation to the respiration of the patient, which in turn moves a ball up and down in a tube to indicate the tidal volume of respiration. This arrangement requires that a plurality of interrelated parts function with each other to obtain the desired end results.

In a similar manner, a review of the disclosure in U.S. Pat. No. 3,789,837 will similarly illustrate a complicated machanical arrangement intended to provide a visual display of tidal volume. In contrast to the above disclosures, I have discovered a substantially simplified system for obtaining a visual readout of tidal volume that additionally has various other advantages over the prior art which will become apparent as the disclosure proceeds.

OBJECTS OF THE INVENTION

An object of the present invention is to provide an improved system for measuring the instantaneous or tidal volume of breathing by a medical patient.

Another object of the present invention is to provide a system in which breath by breath readout of tidal volumes directed toward the patient is visually displayed.

Another object of the present invention is to provide a breathing system convenient for optimizing of flow rates and inhalation time to the patient's benefit without repeated calculations to monitor the effects of interrelated changes in tidal volume.

Another object of the present invention is to provide a timed-flow volume ventilator in which the effects of changes in altitude and gas composition on tidal volume are automically corrected in the readout.

Another object of the present invention is to provide a breathing system in which accurate timing control is unnecessary and the exhalation programming system can be manually regulated via an observation of the instantly indicated tidal volume.

Another object of the present invention is to provide concurrent readout of tidal volumes in relation to patient breathing pressures at more than one time interval to provide a convenient accumulation of data for calculating the patient's pulmonary compliance.

Other objects and advantages of the present invention will become apparent as the disclosure proceeds.

SUMMARY OF THE INVENTION

The outstanding and unexpected results obtained by the practice of the method and apparatus of this invention are obtained by a series of features, steps, and elements assembled and working together in interrelated combination. The breath volume indicating method and system of the present invention includes a regulator for controlling the flow of gas from a source of gas under pressure to a supply system for delivery of the gas under pressure to a patient and to a chamber providing a fixed volume to receive a supply of the gas therein.

Flow orifices are connected in operative relation to the regulator. The flow orifices are calibrated to provide proportional flows of gas to the supply system and to the chamber from th regulator. Values are operatively associated with the supply system and the chamber and are operable between closed and open positions. The closed position generally coincides with an inhalation period of the patient so as to obtain a flow of the gas to the patient and into the chamber concurrently. The open position generally coincides with the exhalation period of the patient so as to obtain patient venting through the supply system and the chamber, concurrently.

A programmer or control is operatively associated with the valves to obtain periodic movement between the open position and the closed position, and a gauge is operatively connected to the chamber such that a tidal volume is indicated on the gauge that is directly equivalent of the volume of the gas directed to the patient through the supply system during the inhalation period when the values are in the closed position.

Accordingly, tidal volume can be measured by regulating the flow of gas from the source of gas under pressure and to the patient as well as to the chamber. By maintaining a proportional flow of the gas to the patient and to the chamber from the source of gas, while controlling the flow of the gas to the patient and to the chamber on an intermittent basis, generally coinciding with the inhalation and exhalation periods of the patient, so as to obtain a flow of the gas to the patient and the chamber concurrently during the inhalation period, and venting the supply of gas and the chamber concurrently during the exhalation period, it is possible to obtain from the gauged increase of pressure in the chamber during each inhalation period a measurement of the tidal volume provided to the patient during each inhalation period.

The procedure for maintaining a proportional flow includes providing a patient orifice and a chamber orifice communicating with each other and a regulated supply of gas from the source. The controlling of the gas flow includes providing a patient valve operatively connected to the regulated supply of gas to the patient and a chamber valve operatively connected to the chamber, with the valves operable between open and closed positions, such that venting of the regulated supply of gas and the chamber to the atmosphere during the open position of each of the valves is obtained.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE DRAWINGS

Figure 1:
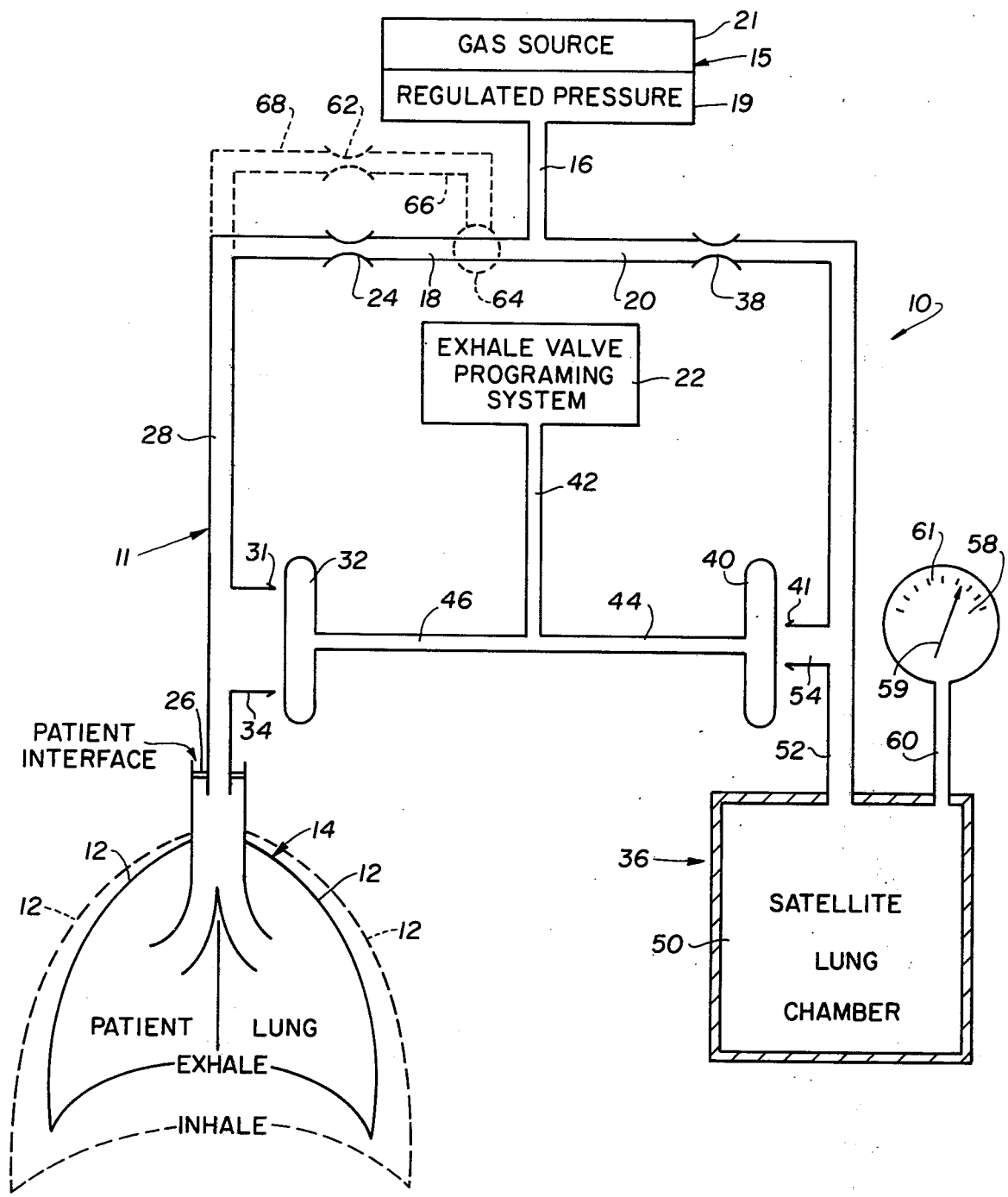
FIG. 1 is a substantially block diagram illustrating the tidal volume display system of the present invention.

Referring to the drawings, there is illustrated in FIG. 1 a preferred embodiment of the present invention which includes a breathing volume indicating device or system 10 for immediate indication of the tidal volume delivered by a timed-flow volume ventilator or supply means 11 to the lungs 12 of a patient 14. The volume of the lungs 12 after the patient exhales is illustrated in the "Exhale" condition, and after that the patient inhales to expand the lungs to the "Inhale" condition as illustrated by broken lines.

Breathing gases enter the typical ventilator supply means 11 from compressed gas cylinders or a central distribution system 15 regulated at approximately 50 p.s.i. gauge pressure. An outlet conduit 16 is connected to the distribution system 15 and branches into conduits 18 and 20. The distribution system 15 includes a flow control system or regulating means 19 and a replaceable source or supply of compressed gas 21 coupled thereto. The regulating means 19 is connected to a fixed patient orifice 24 by means of branch conduit 18.

Exhalation control or programming means system 22 is provided and can be any one of several designs whose details are not pertinent to the function of the subject tidal volume display system 10 as long as it can provide an adjustable time for loading and unloading of a pneumatically controlled exhalation patient valve 32.

The adjustable steady state flow issuing from the patient flow control orifice 24 flows to the patient interface 26 by conduit 28 where it either enters the patient's lungs 12 or exits to ambient air through a vent 31 which is operatively associated with the exhalation patient valve 32, as a function of the programmed condition of the exhalation valve 32. When the programming system 22 calls for inhalation, the exhalation valve 32 is pneumatically shut into a closed position and remains shut for the inhalation time selected. During this period of time when the valve 32 is in the closed position, the vent 31 is closed to force the gas into the lungs 12 of the patient 14. When the programming means 22 calls for exhalation, the valve 32 is unloaded or brought into an open position, and vent 31 is opened and flow from the patient lungs 12 plus flow from orifice 24 are vented to ambient.

The regulating means 19 includes a pressure regulator that is conventional in design and is used to reduce the 50 p.s.i. inlet pressure from the supply source 21 to some steady pressure between zero and 50 p.s.i. as a function of manual adjustment made on the pressure control that may be incorporated within the distribution system 15. The exhalation valve 32 is of standard commercial design well known in the art which provides an elastic capsule which can be pneumatically directed toward or away from the vent or valve seat 31. The patient orifice 24 is fixed in its functional mode, but is typically designed to be adjustable for initial calibration purposes. Conduit 34 connects valve seat 31 to conduit 28.

The flow delivered toward the patient will be a function of the area of the opening in the orifice 24 and the upstream absolute pressure and the density of gases flowing, and possibly the absolute pressure downstream of the orifice 24. A regulator (not shown) forming part of the system 15 uses ambient pressure as a reference, and its regulated absolute pressure will change with changes in ambient absolute pressure such as would occur with an altitude change. Gas density also changes as a function of absolute pressure and the effect of altitude becomes part of any accurate tidal volume determination derived from a flow time calculation. Gas composition also affects density, but density differences between the primary gases (oxygen and air) over the range of typical mixture is small enough to be ignored in most cases.

If the regulated orifice upstream pressure is low, the downstream pressure (delivered to the patient) can affect the flow through the patient orifice 24 and thereby become a part of any flow measurement or calculation. However, there is a law of fluid physics that states that when the ratio of orifice upstream absolute pressure to orifice downstream absolute pressure exceeds 1.9, gas velocity through the orifice is maximized and flow becomes dependent on the absolute upstream pressure only. If the maximum pressure to be delivered to the patient is 50 mm Hg. (68 cm water), then the flow condition that will be independent of downstream conditions at sea level will occur at an absolute upstream pressure of 50 plus 760 mm Hg. times 1.9 or 1540 mm Hg. absolute (780 mm or 15 p.s.i. gauge). This suggests that for accurate flow calibration and calculation, the pressure regulator adjustment in the regulating means 19 should be limited within a range of 15 to 50 p.s.i.

The subject invention introduces an analogue into the system that is exposed to the same absolute pressures and exhalation program times as the above discussed patient directed components of the system 10. The analogue will be referred to as the satellite means or system 36. The satellite means 36 includes satellite or chamber flow orifice 38 which may be equal in function with patient orifice 24, and the satellite exhalation or chamber valve 40, equal in function to the patient valve 32. The upstream side of satellite orifice 38 is exposed to the patient orifice 24 upstream pressure via a direct connection of branch conduits 18 and 20 into the patient flow system. The chamber valve 40 is controlled via a direct connection between conduits 42 and 44 to the patient pneumatic exhalation control or programming means system 22. Conduit 46 is connected to conduits 42 and 44 at one end and patient valve 32 at the opposite end.

The satellite means 36 includes a lung or chamber means 50 that is a patient lung analogue only in its mechanical function; its physical structure and cyclic pressure excursions are different. The chamber means 50 is a sealed rigid volume which is dimensionally stable and is of a convenient size (typically 100 ml internal volume). The chamber means 50 is connected by conduits 52 and 54 to exhalation chamber valve 40. The satellite lung 50 is vented to ambient through its exhalation valve 40 which has a vent 41 associated therewith, and is illustrated in the open position. When the program system 22 closes the valve 40 for an inhalation cycle, the vent 41 is closed. When the vent 41 is in its closed position, gas flow will enter the satellite lung 50 and pressure will build up in the satellite lung 50 as a function of orifice 38 size (area), upstream absolute pressure, time in the inhalation mode and satellite lung 50 volume.

If the satellite lung 50 volume and orifice 38 area are properly calibrated, the pressure build-up will have a known direct relation to the volume of gas that has flowed into the satellite system 36 and into patient supply system 11 during the inhale time period and can be read out as volume on a pressure gauge means 58 that is connected by conduit 60 to the satellite lung 50. Furthermore, the fixed volume of the chamber means 50 is smaller than the ambient volume of gas per inhalation by a patient 14 using the device during each inhalation cycle or period. In this manner an increase in measurable pressure, i.e. in a quantitative (quantifiable) amount, in the chamber means 50 during each inhalation period is obtained, which increase in measurable pressure is analogous to the volume of the gas supplied to the patient, and this pressure increase is displayable on the gauge means 58.

Furthermore, since the pressure upstream of the satellite orifice 38 is identical to the pressure upstream of the patient orifice 24 and the closing time of the two exhalation valves 32 and 40 is the same, the volume indicated on the gauge 58 will be directly related to the volume directed to the patient and the satellite gauge means 58 can be calibrated in tidal volume delivered to the patient. The chamber means 50 is small, and its system can be easily calibrated, made leak tight, and be expected to remain stable in contrast to the highly variable patient's lung system. The gauge means 58 may include a dial 59 and a calibrated scale 61 thereon, such that a visual indication of the tidal volume is displayed.

There are limits to the pressure rise if a linear pressure volume calibration is to be obtained. There is a need to maintain an upstream absolute pressure more than 1.9 times the absolute downstream pressure applied to the satellite system 36 for the reason previously discussed in describing the patient system. For any one class of patients a maximum tidal volume can be established, and from this a maximum satellite design pressure compatible with the 1.9 absolute pressure ratio can be determined.

For example, when applying a ventilator to a neonatal infant, a maximum expected tidal volume might be 100 ml and the maximum flow and time might be 100 ml/second and 1.0 second. The infant patient orifice 24 would then be calibrated to pass 100 ml/sec., at an upstream pressure of 50 p.s.i., which is maximum available from the standard inlet pressure. If a commercial pressure gauge with a standard 10 p.s.i. range is chosen for the tidal volume gauge means 58, the a safe calibration might be to set the satellite orifice 38 to allow 6.0 p.s.i. pressure build-up in the satellite system 36 at 50 p.s.i. (65 p.s.i. absolute) upstream pressure in one second and the readout could be marked as 100 ml tidal volume.

If the regulated pressure is then dropped to 17.5 p.s.i. gauge (32.5 absolute), the patient flow rate will drop to 50 ml/sec. and a corresponding satellite one second pressure of 3.0 p.s.i. (18 absolute) would indicate 50 ml tidal volume. Under these one half flow and tidal volume settings, the absolute pressure ratio will be 32.5/18 or 1.8, which is just below the point where downstream pressure will begin to influence flow through chamber orifice 38, which suggests that the pressure adjustments on the regulator within the regulating means 19 be kept between 17.5 p.s.i. at 50 p.s.i. gauge and that tidal volumes lower than 50 ml be accomplished by shorter inspiratory time intervals.

There will be situations where a greater or lesser flow and tidal volume range should be made available than is afforded by the above discussed 17.5 to 50 p.s.i. adjustment range. This is easily accomplished by adding an additional patient flow orifice 62 and a range selector valve 64, as shown in broken lines on FIG. 1. Now if the range selector 64 diverts patient gas flow through range flow orifice 62, by means of conduit 66 extending between range selector 64 and range flow orifice 62, conduit 68 connects the flow orifice valve 62 to conduit 28. If the range flow orifice 62 is one half the area of patient orifice 24, then the flows will be one half and an additional low range scale of one half tidal voluem could be added as an additional scale to the tidal volume indicating gauge means 58. Addition of an extra flow range does not require a change in the satellite systems flow time-pressure components or calibration, it only requires the addition of another tidal volume readout scale on the gauge means 58.

Accordingly, the provision of a respiratory ventilator system 11 having a parallel satellite lung system 36 that can be calibrated to give a direct and simultaneous indication of the tidal volume, that is, the volume of gas delivered by the ventilator system, it obtainable as disclosed above. The patient and chamber flow orifices 24 and 38, respectively, remain open at all times during operation of the system 10. The patient and chamber exhalation valves 32 and 40, respectively, operate concurrently with each other, and may be activated by gas under pressure applied by the control means 22.

The satellite system 36 will experience a pressure build-up that will vary as a function of the orifice area, the upstream absolute pressure, the time of inhalation, and the volume of the chamber means 50. Provided the lung volume and orifice area are properly calibrated, the pressure build-up will have a known direct relation to the volume of gas that has flowed into the satellite system 36 during the inhale time and can be read out as a volume on the pressure gauge means 58.

Furthermore, since the pressure upstream of the chamber orifice 38 is identical to the pressure upstream of the patient orifice 24, and the closing time of the two exhalation valves 32 and 40 is the same, the volume indicated on the gauge means 58 will be directly related to the volume directed to the patient and the satellite gauge means 58 can be calibrated in tidal volume delivered to the patient.

In the manner described the breathing volume indicating system 10 includes regulating means 19 for controlling the flow of gas from a source of gas 21 under pressure, with the supply means 11 operatively coupled to the regulating means 19 for delivery of gas under pressure to a patient 14. The chamber means 50 is operatively coupled to the regulating means 19 and is of a rigid fixed volume being adaptable to receive a supply of the gas therein. The flow orifice means being comprised of orifices 24 and 38, is in operative relation to the regulating means 19, with the flow orifice means being calibrated to provide a proportional flow of gas under the same pressure to the supply means 11 and the chamber means 50 from the regulating means 19.

The valve means being comprised of valves 32 and 40, is operatively associated with the supply means 11 and the chamber means 50. The valve means is operable between closed and open positions, with the closed position generally coinciding with an inhalation period of the patient 14 so as to obtain a flow of the gas to the patient and into the chamber means 50 concurrently. The open position generally coincides with the exhalation period of the patient so as to obtain venting of the supply means 11 and the chamber means 50 concurrently.

The programming means 22 is operatively associated with the valve means so as to obtain periodic movement of the valves 32 and 40 between the open position and the closed position. The gauge means is operatively connected to the chamber means 50 such that a tidal volume is indicated on the gauge means 58 that is directly equivalent of the volume of the gas directed to the patient 14 through the supply means 11 during the inhalation period when the valve means is in the closed position.

By adding the additional patient flow orifice 62 and a range selector valve 64, different tidal volume delivery ranges can be provided and these ranges can be accommodated on the indicating gauge means 58 by the provision of additional scales on the face of the gauge.

Pressures within the tidal volume display system 10 during inhalation are preferably higher than pressures within ventilator system 11. Area of satellite orifice 38 and its proportional flow is preferably smaller than the area and flow of patient orifice 24. The area of valve seat 31 of patient valve 32 is preferably larger than the area of valve seat 41 of the chamber valve 40 in substantial harmony with pressure and flow proportionality between systems 11 and 10. At the completion of each venting cycle the satellite lung 50 will have an initial internal pressure which may be equal to ambient pressure.

Although an illustrative embodiment of the invention has been described in detail herein with reference to the accompanying drawing, it is to be understood that the invention is not limited to the precise embodiment and that various changes and modifications may be effected therein without departing from the scope or spirit of the invention.

I claim:

1. A method of indicating the volume of gas supplied to a patient, comprising the steps of:
   A. supplying a flow of gas under pressure to a patient from a supply of gas,
   B. providing a fixed volume chamber operatively coupled to said supply of gas to receive another flow of said gas therein,
   C. controlling said flows of said gas to the patient and to said chamber on an intermittent basis generally coinciding with the inhalation and exhalation periods of the patient, and proportioning said flows, so as to obtain proportional flows of said gas to the patient and into said chamber concurrently during the inhalation period and a venting of said supply of gas and said chamber concurrently to an initial pressure during the exhalation period, and
   D. gauging the increase of pressure over said initial pressure in said chamber during each inhalation period so as to obtain a measurement of the tidal volume provided to the patient during each inhalation period.

2. The method as set forth in claim 1, and further comprising the step of displaying visually the tidal volume gauged from the increase of pressure in said chamber.

3. The method as set forth in claim 1, and further comprising the step of selecting the fixed volume of said chamber as smaller than the volume of said gas supplied per inhalation to a patient, so as to obtain a quantitative increase in the pressure in said chamber during each inhalation period that is analogous to the volume of said gas inhaled by the patient.

4. The method as set forth in claim 1, wherein said step of controlling said flows of said gas includes the step of providing a patient valve operatively connected to said supply of gas to the patient and a chamber valve operatively connected to said chamber, said valves being operable between open and closed positions such that venting of said supply of gas and said chamber to the atmosphere during said open position of each of said valves is obtained.

5. A method of indicating the volume of gas supplied to a patient, comprising the steps of:
   A. regulating the flow of gas from a supply of gas under pressure,
   B. supplying a flow of said gas to the patient from said regulated supply of gas,
   C. providing a fixed volume chamber operatively coupled to said regulated supply of gas to receive another flow of said gas from said supply of said gas therein,
   D. proportioning said flows of said regulated supply of gas to the patient and to said chamber,
   E. controlling said flows of said regulated supply of gas to the patient and to said chamber on an intermittent basis generally conciding with the inhalation and exhalation periods fo the patient, so as to obtain said flows of said regulated supply of gas to the patient and said chamber concurrently during the inhalation period and a venting of said regulated supply of gas and said chamber to atmosphere concurrently during the exhalation period, and
   F. gauging the increase of pressure in said chamber during each inhalation period so as to obtain a measurement of the tidal volume provided to the patient during each inhalation period.

6. The method as set forth in claim 5, and further comprising the step of displaying visually the tidal volume gauged from the increase of pressure in said chamber.

7. The method of indicating the tidal volume of gas directed to a patient per inhalation period, comprising the steps of:
   A. concurrently supplying a gas proportionally to a patient and to a satellite lung during each inhalation period, said satellite lung having a predetermined fixed volume and initial internal pressure, and
   B. converting the increase of pressure over said initial internal pressure in said satellite lung during said inhalation period to a visual indication corresponding to the tidal volume of said gas directed to the patient in an inhalation period.

8. The method as set forth in claim 7, and including the step of regulating the supply of gas to the patient and said satellite lung at proportional pressures and rates of flow.

9. The method as set forth in claim 7, and further comprising the step of venting said satellite lung to said initial pressure during the exhalation period of the patient.

10. A breath volume indicating device comprising:
  A. supply means for delivery of gas under pressure to a patient,
  B. chamber means operatively associated with said supply means and providing a fixed volume for receiving a supply of said gas therein proportional to that delivered to said patient,
  C. valve means operatively associated with said supply means and said chamber means and operable between closed and open positions for obtaining while said valve means is in said closed position which generally coincides with an inhalation period of the patient flows of said gas to the patient and into said chamber means concurrently, and while said valve means is in said open position which generally coincides with an exhalation period of the patient venting of said supply means and said chamber means concurrently to an initial pressure, and
  D. gauge means operatively connected to said chamber means for responding to the increase in pressure from said initial pressure in said chamber means while said valve means is in said closed position such that a tidal volume is indicated on said gauge means that is directed related to the volume of said gas delivered to the patient while said valve means is in said closed position.

11. A breath volume indicating device as in claim 10, and further comprising a gas source at regulated pressure coupled to said supply means.

12. A breath volume indicating device as in claim 10, and further comprising a source of said gas under pressure and regulating means for controlling the flow of gas to said supply means and to said chamber means from said source of gas under pressure.

13. A breath volume indicating device as in claim 10, and further comprising control means operatively associated with said valve means for periodically operating said valve means between said open position and said closed position during periods generally coinciding with successive said inhalation and exhalation periods.

14. A breath volume indicating device as in claim 13, wherein said control means operates said valve means with gas under pressure.

15. A breath volume indicating device as in claim 13, wherein said valve means comprises a patient valve operatively connected to said supply means and a chamber valve operatively connected to said chamber means.

16. A breath volume indicating device as in claim 15, wherein said control means is operatively coupled to each of said valves for controlling same.

17. A breath volume indicating device as in claim 15, wherein said patient valve and said chamber valve each has a valve seat means for venting said gas from said supply means and said chamber means to the atmosphere when each of said valves is in said open position.

18. A breath volume indicating device as in claim 17, wherein said valve seat means of said patient valve is larger than said valve seat means of said chamber valve whereby said chamber means can be kept small.

19. A breath volume indicating device as in claim 10, and further comprising varying means for varying the volume of said gas delivered by said supply means during successive closed positions of said valve means.

20. A breath volume indicating device as in claim 19, wherein said varying means includes a pressure selector valve variable over a range and a flow orifice variable over a range successively coupled to said supply means.

21. A breath volume indicating device as in claim 10, and further comprising flow orifice means in communicating relation to said supply means and said chamber means for providing substantially equal flows of gas from equal pressure to said supply means and said chamber means.

22. A breath volume indicating device as in claim 21, wherein said flow orifice means includes a patient orifice and a chamber orifice communicating with each other and a source of said gas and coupled to said supply means and said chamber means, respectively.

23. A breath volume indicating device as in claim 10, wherein said gauge means indicates said tidal volume visually.

24. A breath volume indicating device as in claim 10, wherein said fixed volume of said chamber means is smaller than the volume of said gas per inhalation delivered to the patient so as to obtain an increase in the pressure in a quantitative amount in said chamber means during each inhalation period that is analogous to the volume of said gas supplied to the patient and displayable on said gauge means.

25. A breathing volume indicating system comprising:
  A. regulating means for controlling the flow of a gas from a source of said gas under pressure,
  B. supply means operatively coupled to said regulating means for delivering said gas under pressure to a patient,
  C. chamber means operatively coupled to said regulating means and providing a fixed volume for receiving a supply of said gas therein proportional to that delivered to the patient,
  D. valve means operatively associated with said supply means and said chamber means and operable between closed and open positions for obtaining while said valve means is in said closed position which generally coincides with each inhalation period of the patient flows of said gas to the patient and into said chamber means concurrently, and while said valve means is in said open position which generally coincides with each exhalation period of the patient venting of said supply means and said chamber means concurrently to atmosphere, and
  E. gauge means operatively connected to said chamber means for responding to the increase in pressure from atmosphere in said chamber means while said valve means is in said closed position such that a tidal volume is indicated on said gauge means that is directly equivalent of the volume of said gas delivered to the patient through said supply means while said valve means is in said closed position.

26. A breathing volume indicating system as in claim 25, and further comprising a gas source under pressure coupled to said regulating means.

27. A breathing volume indicating system as in claim 25, including programming means operatively associated with said valve means for operating said valve means between said open position and said closed position in periods generally coinciding with successive inhalation and exhalation periods.

28. A breathing volume indicating system as in claim 27, wherein said valve means is operated by gas under pressure.

29. A breathing volume indicating system as in claim 27, wherein said valve means includes a patient valve operatively connected to said supply means and a chamber valve operatively connected to said chamber means.

30. A breathing volume indicating system as in claim 29, said programming means is operatively coupled to each of said valves for controlling same.

31. A breathing volume indicating system as in claim 29, wherein said patient valve and said chamber valve each include valve seat means for venting said gas from said supply means and said chamber means to the atmosphere during said open position of each of said valves.

32. A breath volume indicating system as in claim 25, and further comprising flow orifice means in communicating relation to said regulating means, said supply means, and said chamber means for providing proportional flows of said gas to said supply means and said chamber means from said regulating means.

33. A breathing volume indicating system as in claim 32, wherein said flow orifice means includes a patient orifice and a chamber orifice communicating with each other and said regulating means and coupled to said supply means and said chamber means, respectively.

34. A breathing volume indicating system comprising:
  A. regulating means for controlling the flow of a gas from a source of said gas under pressure,
  B. supply means operatively coupled to said regulating means for delivering said gas under pressure to a patient,
  C. chamber means operatively coupled to said regulating means and providing a fixed volume for receiving a supply of said gas therein,
  D. flow orifice means in operative relation to said regulating means, said supply means and said chamber means for providing proportional flows of said gas to said supply means and said chamber means from said regulating means,
  E. valve means operatively associated with said supply means and said chamber means and operable between closed and open positions for obtaining while said valve means is in said closed position which generally coincides with each inhalation period of the patient flows of said gas to the patient and into said chamber means concurrently, and while said valve means is in said open position which generally coincides with each exhalation period of the patient venting of said supply means and said chamber means means concurrently to atmospheric pressure,
  F. programming means operatively associated with said valve means for obtaining periodic movement of said valve means between said open position and said closed position in periods generally coinciding with said inhalation and exhalation periods of the patient, and
  G. gauge means operatively connected to said chamber means and responsive to the increase pressure in said chamber means over said atmospheric pressure while said valve means is in said closed position for indicating a tidal volume that is directly equivalent of the volume of said gas delivered to the patient through said supply means while said valve means is in said closed position.

35. A breathing volume indicating system as in claim 34, wherein said gauge means comprises means for visually indicating said tidal volume.

36. A breathing volume indicating system as in claim 34, wherein said flow orifice means includes a patient orifice and a chamber orifice communicating with each other and said regulating means and coupled to said supply means and said chamber means, respectively.

37. A breathing volume indicating system as in claim 34, wherein said valve means includes a patient valve operatively connected to said supply means and a chamber valve operatively connected to said chamber means, and said programming means is operatively coupled to each of said valves for controlling same.

38. A breathing volume indicating system as in claim 37, wherein said patient valve and said chamber valve each include a valve seat means for venting of said gas from said supply means and said chamber means to the atmosphere while said valve means is in said open position.

39. A breathing volume indicating system as in claim 38, wherein said valve means is activated by gas under pressure supplied by said programming means.

40. Apparatus for indicating the tidal volume of gas delivered to a patient per inhalation period, comprising:
  a satellite lung having a pre-determined fixed volume and initial internal pressure,
    means for concurrently supplying gas to a patient and to said satellite lung during an inhalation period of the patient, and
    means for converting the pressure increase over said initial internal pressure in said satellite lung during said inhalation period into a visual indication corresponding to the tidal volume of said gas supplied to the patient in said inhalation period.

41. Apparatus as in claim 40, and further comprising means for regulating the supply of gas to the patient and said satellite lung at substantially the same pressure and rate of flow.

42. Apparatus as in claim 40, and further comprising means for venting said satellite lung to said initial internal pressure during an exhalation period of the patient.

43. Apparatus as in claim 42, and further comprising means for programming said venting means on an intermittent basis coinciding with successive exhalation periods of the patient.

44. Apparatus as in claim 43, wherein said venting and programming means further comprises means for concurrently venting said supply of gas to the patient.

* * * * *